United States Patent
Yoshizawa et al.

(10) Patent No.: US 9,179,894 B2
(45) Date of Patent: Nov. 10, 2015

(54) ULTRASONIC DIAGNOSIS APPARATUS (75) Inventors: Shingo Yoshizawa, Mitaka (JP);
Masanori Hisatsu, Mitaka (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 830 days.

(21) Appl. No.: 13/251,514

(22) Filed: Oct. 3, 2011

(65) Prior Publication Data
US 2012/0095346 A1 Apr. 19, 2012

(30) Foreign Application Priority Data

Oct. 13, 2010 (JP) ................................. 2010-230404
Apr. 21, 2011 (JP) ................................. 2011-095018

(51) Int. Cl.
*A61B 8/08* (2006.01)
*G10K 11/34* (2006.01)
*G01S 15/89* (2006.01)
*G01S 7/52* (2006.01)

(52) U.S. Cl.
CPC ........... *A61B 8/5269* (2013.01); *G01S 7/52047* (2013.01); *G01S 7/52077* (2013.01); *G01S 15/8915* (2013.01); *G10K 11/346* (2013.01); *G01S 7/52033* (2013.01); *G01S 7/52049* (2013.01)

(58) Field of Classification Search
CPC ...... A61B 5/02; A61B 5/021; A61B 5/02125; A61B 5/02405; A61B 5/0285
See application file for complete search history.

(56) References Cited

U.S. PATENT DOCUMENTS

2005/0033165 A1    2/2005    Ustuner et al.

FOREIGN PATENT DOCUMENTS

| JP | 6-105841 A | 4/1994 |
|---|---|---|
| JP | 2006-217943 A | 8/2006 |
| JP | 2009-213565 A | 9/2009 |
| WO | 2010/018282 A1 | 2/2010 |
| WO | 2011/095896 A1 | 8/2011 |

OTHER PUBLICATIONS

Camacho, Jorge et al., "Phase Coherence Imaging", IEEE Transactions on Ultrasonics, Ferroelectrics, and Frequency Control, May 2009, p. 958-974, vol. 56.

Pai-Chi Li, et al, "Adaptive Imaging Using the Generalized Coherence Factor", IEEE Transactions on Ultrasonics, Ferroelectrics, and Frequency Control, vol. 50, No. 2, Feb. 1, 2003, pp. 128-141, Cited in European Search Report. (14 pages).

(Continued)

*Primary Examiner* — Unsu Jung
*Assistant Examiner* — Saurel J Selkin
(74) *Attorney, Agent, or Firm* — Westerman, Hattori, Daniels & Adrian, LLP (57) ABSTRACT

There is provided an ultrasonic diagnosis apparatus capable of reducing an unnecessary signal component in a reception signal. A sign data array formed of a plurality of sign data items arranged in an element arranging direction is extracted from a plurality of element reception signals having been subjected to delay processing but having not been subjected to summing processing. A factor computing unit computes a first factor indicating a level of sign coherence in the sign data array and a second factor indicating a sign transit density in the sign data array. The factor computing unit then computes a factor (evaluation value) for adjusting gain of the reception signal, based on the first factor and the second factor.

8 Claims, 8 Drawing Sheets

(56) References Cited

OTHER PUBLICATIONS

European Search Report, dated Feb. 22, 2012, issued in corresponding European Patent Application No. 11007976.1-2319.

Japanese Office Action dated Mar. 18, 2014, issued in corresponding Japanese Patent Application No. 2010-230404 (2 pages).

Camacho J. et al., "Grating-lobes reduction by application of Phase Coherence Factors", IEEE International Ultrasonics Symposium, vol. 1, pp. 341-344, (2009), cited in Japanese Office Action dated Mar. 18, 2014, issued in corresponding Japanese Patent Application No. 2010-230404.

| CASE | STATUS | | | EVALUATION | |
|---|---|---|---|---|---|
| | COMPONENT RATIO | AMPLITUDE PROFILE OF MAIN-LOBE COMPONENT | ZERO CROSS FREQUENCY GENERATED BY SIDE-LOBE COMPONENT | SCF | STF |
| 1 (FIG.3.(A)) | MAIN-LOBE COMPONENT IS DOMINANT | DISTANT FROM ±π/2(BASELINE) | — | PROPER (IDENTIFIED THAT PHASES ARE IDENTICAL) | PROPER (IDENTIFIED THAT PHASES ARE IDENTICAL) |
| 2 (FIG.3.(B)) | MAIN-LOBE COMPONENT IS DOMINANT | IN THE VICINITY OF ±π/2(BASELINE) | — | IMPROPER (MISIDENTIFIED THAT PHASES ARE TURBULENT) | PROPER (IDENTIFIED THAT PHASES ARE IDENTICAL) |
| 3 (FIG.4.(A)) | SIDE-LOBE COMPONENT IS SLIGHTLY MORE THAN MAIN-LOBE COMPONENT | — | LOW | PROPER (IDENTIFIED THAT PHASES ARE SOMEWHAT TURBULENT) | IMPROPER (MISIDENTIFIED THAT PHASES ARE IDENTICAL) |
| 4 (FIG.4.(B)) | SIDE-LOBE COMPONENT IS SLIGHTLY MORE THAN MAIN-LOBE COMPONENT | — | HIGH | PROPER (IDENTIFIED THAT PHASES ARE SOMEWHAT TURBULENT) | IMPROPER (MISIDENTIFIED THAT PHASES ARE TURBULENT) |
| 5 (FIG.5.(A)) | SIDE-LOBE COMPONENT IS DOMINANT | — | LOW | PROPER (IDENTIFIED THAT PHASES ARE TURBULENT) | IMPROPER (MISIDENTIFIED THAT PHASES ARE IDENTICAL) |
| 6 (FIG.5.(B)) | SIDE-LOBE COMPONENT IS DOMINANT | — | HIGH | PROPER (IDENTIFIED THAT PHASES ARE TURBULENT) | PROPER (IDENTIFIED THAT PHASES ARE TURBULENT) |

ULTRASONIC DIAGNOSIS APPARATUS

BACKGROUND

1. Technical Field

The present invention relates to an ultrasonic diagnosis apparatus, and more particularly to a technique of reducing an unnecessary or undesired signal component such as a side-lobe component, a grating lobe component, or the like, contained in a reception signal.

2. Background Art

Ultrasonic diagnosis apparatuses are apparatuses which form an ultrasonic diagnosis image by transmitting and receiving ultrasound to and from a living organism. In order to increase the image quality of the ultrasonic diagnosis image, it is desirable to reduce an unnecessary signal component contained in a reception signal; i.e., a side-lobe component, a grating lobe component, a noise component, or the like.

More specifically, in a receiving beam former provided in an ultrasonic diagnosis apparatus, for the purpose of focusing, delay processing (phase alignment processing) is applied to a plurality of element reception signals supplied from a plurality of transducer elements, and thereafter, summing processing is further applied to the plurality of element reception signals having been subjected to the delay processing. With these processing operations, beam data serving as an RF signal, for use in forming an ultrasonic image, are obtained. When reflection waves are received from a focus point, as phases are identical among the plurality of element reception signals having been subjected to the delay processing, beam data having large amplitude can be obtained after the summing processing. In contrast, in the case of reflection waves from a point other than the focus point, as the phases are not identical among the plurality of element reception signals, only beam data having low amplitude can be obtained. However, the beam data actually contain an unnecessary signal component such as a side-lobe component.

As a method for suppressing an unnecessary signal component contained in a reception signal, a method for suppressing a reception signal by using a factor, called SCF (Sign Coherence Factor), has been proposed. According to this method, based on a sign data array which is formed of a plurality of sign data items arranged in the element arrangement direction, which are extracted from a plurality of element reception signals having been subjected to the delay processing but having not yet been subjected to the summing processing, the gain of a reception signal (beam data) after the summing processing is adjusted. Specifically, the gain is adjusted in accordance with SCF, which is defined based on the ratio of the number of positive sign data items and the number of negative sign data items (see Jorge Camacho, et al, "Phase Coherence Imaging", IEEE Transactions Ultrasonics, vol. 56, No. 5, 2009 (WO2010/018282)).

However, if the SCF method described above is always applied, there may be a possibility that a main lobe component is excessively suppressed, thereby reducing the image quality of an ultrasonic image. Specifically, according to the above SCF method, in which only the number of positive sign data items and the number of negative sign data items are referenced, the gain control is not based on the amplitude of the individual element reception signals and the amplitude profile formed of a plurality of instantaneous amplitude values of the plurality of element reception signals. Accordingly, with the SCF method, there is a possibility that turbulence of the phase is misidentified when the amplitude profile changes across the baseline, despite the amplitude profiles being identical to a certain degree.

SUMMARY

An advantage of the present invention is to prevent excessive suppression with respect to a reception signal while reducing an unnecessary signal component contained in the reception signal.

Another advantage of the present invention is to comprehensively specify and reduce an unnecessary signal component.

In accordance with an aspect of the invention, there is provided an ultrasonic diagnosis apparatus including an array transducer which is composed of a plurality of transducer elements; a delay processing unit which performs delay processing with respect to a plurality of element reception signals output from the plurality of transducer elements; a summing processing unit which performs summing processing with respect to the plurality of element reception signals having been subjected to the delay processing; a computing unit which computes an evaluation value based on a sign data array formed of a plurality of sign data items arranged in an element arranging direction, that are extracted from the plurality of element reception signals having been subjected to the delay processing but having not been subjected to the summing processing, the computing unit computing the evaluation value based on a first factor and a second factor which are different from each other, the first factor and the second factor being computed from the sign data array; and a gain adjustment unit which adjusts gain of a reception signal having been subjected to the summing processing, by using the evaluation value.

With the above structure, the gain of a reception signal after phase alignment and summing processing is adjusted based on an evaluation value. In this case, as the evaluation value is computed based on a first factor and a second factor which reflect the content or structure of a sign data array and which differ from each other, more suitable evaluation value computation in accordance with a situation can be performed as compared with the case where an evaluation value is computed based only on one of these factors. As the first factor and the second factor are computed from the same sign data array, advantages of a reduction in the amount of computation and simplification of the structure can be obtained.

Preferably, the first factor represents a level of sign coherence in the sign data array, and the second factor represents a sign transit density in the sign data array. An evaluation value is computed based on these two factors.

When computing the evaluation value only with reference to the sign coherence, the level of the amplitude of each element reception signal and the arranging state of the sign data in the channel direction are not considered. Accordingly, there are cases in which phases are misidentified as being turbulent despite being identical. Further, in the case of computing the evaluation value only with reference to the sign transit density, as the sign transit density changes in accordance with the positional relationship between the strong reflector and the receiving beam origin, there is a possibility that turbulence of phase is misidentified. By referring to both the sign coherence and the sign transit density, the misidentification described above can be prevented or reduced.

The ratio of existence of the positive sign data and the negative sign data in a sign data array may be computed as the level of sign coherence. If a sign data array is composed of only one of the positive sign data and the negative sign data, for example, the level of sign coherence is maximum. On the other hand, if a sign data array is composed of the same number of the positive sign data items and the negative sign data items, the level of sign coherence is minimum. Conversely, the degree of variation of the sign data or the degree of diversity of the sign data may be computed as the level of sign coherence. As the sign transit density, the number of sign inversion events in a sign data array or the frequency of sign inversion may be computed. When a larger number of sign inversion points exist along the channel direction, for example, the sign transit density is determined to be large. When only a small number of sign inversion points exist along the channel direction, on the other hand, the sign transit density is determined to be small. Conversely, a value indicating how many times data with the same sign successively appear along the channel direction may be computed as the sign transit density.

Preferably, the computing unit includes a first factor computing unit which computes the first factor with reference to the sign data array, a second factor computing unit which computes the second factor with reference to the sign data array, and an evaluation value computing unit which computes the evaluation value based on the first factor and the second factor. Preferably, the first factor computing unit and the second factor computing unit operate in parallel.

Preferably, the evaluation value computing unit computes the evaluation value by performing weighted addition processing using the first factor and the second factor. Preferably, the evaluation value computing unit computes the evaluation value by performing multiplication processing using the first factor and the second factor. Preferably, in a specific case in which the first factor is smaller than a first threshold value and the second factor is greater than a second threshold value, the evaluation value computing unit determines, as the second factor, a value which is based on the second factor, or a predetermined value. Preferably, the evaluation value computing unit computes the evaluation value in accordance with a dynamic change of a depth of a receiving sample point in real time, for each depth of the receiving sample point.

While, for observation of the sign coherence, it is desirable to use the equation (2) which will be described below, other calculation equations can be used, so long as a variation of the sign can be computed. Similarly, for observation of the sign transit density, while it is desirable to use the equation (4) which will be described below, other calculation equations can be used, so long as the number or frequency of sign inversion can be computed. It is desirable to perform binarization processing with respect to each sign data item prior to the computation of these indicators.

Preferably, a binarization processing unit is shared for computing the two factors. The sign data array may be formed by extracting sign bits from a plurality of sign bits representing each element reception signal.

BRIEF DESCRIPTION OF THE DRAWINGS

A preferred embodiment of the present invention will be described in detail based on the following figures, wherein.

DESCRIPTION OF PREFERRED EMBODIMENTS

A preferred embodiment of the present invention will be described in detail with reference to the accompanying drawings.

An ultrasonic diagnosis apparatus according to the present embodiment suppresses an unnecessary or undesired signal component based on an SCF (Sign Coherence Factor) which has been already described above and an STF (Sign Transit Factor) which will be described below. In other words, two methods are used in combination (or selectively). Here, the two methods which are used are not limited to the SCF method and the STF method. By computing an evaluation value on the basis of a plurality of factors which are obtained from different points of view, the content of the evaluation value can be made more appropriate.

In the following description, a sign data array is formed of a plurality of sign data items which are extracted from a plurality of element reception signals having been subjected to delay processing but not yet having been subjected to summing processing. Each element reception signal is formed of a plurality of echo values (amplitude values) arranged in the depth direction.

(1) Explanation of SCF Method and STF Method

The SCF method is a method for suppressing an unnecessary signal component based on an SCF (Sign Coherence Factor) which is a first factor, and the STF method is a method for suppressing an unnecessary signal component based on an STF (Sign Transit Factor) which is a second factor.

The SCF method will be described first. The SCF is an indicator reflecting the number of the positive sign data items and the number of the negative sign data items in a sign data array or the ratio of existence thereof. Assuming that the depth is "k" and the channel number is "i," an echo value at each depth or a sign bit "si(k)" extracted therefrom is subjected to binarization processing as in the following equation (1):

$$b_i(k) = \begin{cases} -1 & \text{if } s_i(k) < 0 \\ +1 & \text{if } s_i(k) \geq 0 \end{cases} \quad (1)$$

As the sign bit can be either 1 or 0, $b_i(k)=+1$ is obtained when the sign bit is 1, and $b_i(k)=-1$ is obtained when the sign bit is 0. However, the sign bit may be used directly for computation of the evaluation value, without application of this binarization processing. It is also possible to set the baseline to a predetermined amplitude level, rather than the zero level, and execute the binarization processing in this state. In the following description, the above-described $b_i(k)$ will be referred to as a polarity parameter.

With the use of this polarity parameter $b_i(k)$, the factor SCF is defined as described in the following equation (2) as an evaluation indicator concerning the degree of turbulence of the phases:

$$SCF(k) = |1 - \sigma(b_i(k))|^p \qquad (2)$$

$$= \left|1 - \sqrt{1 - \left\{\frac{1}{N}\sum_{i=1}^{N} b_i(k)\right\}^2}\right|^p$$

$$(0 \leq SCF(k) \leq 1)$$

In the above equation, N represents the number of receiving channels, which can be varied depending on a receiving aperture, and p is a variable constant used for adjusting the SCF. $\sigma(bi(k))$ represents a degree of variation of the polarity parameter $b_i(k)$. Accordingly, $1-\sigma(bi(k))$ represents a degree of sign coherence concerning a sign data array. The factor SCF is defined for each depth k.

When the phases are identical among all the receiving channels, as the polarity parameters are identical for all the channels, the SCF results in 1. On the other hand, when the phases become turbulent among the receiving channels, which also results in turbulence of polarities, the SCF approaches 0. Accordingly, by using the SCF to apply weighting to a reception signal (beam data) having been subjected to the phase alignment and summing processing, it is possible to reduce an unnecessary signal component such as a side-lobe component.

However, it has been confirmed by experiments that an "uneven phenomenon" in which a large number of dark portions are generated in a homogeneous medium (e.g. a portion in an interior of an organ or the like packed with tissues) is likely to occur when the suppression processing is performed only with the use of the SCF. The reasons for this will be described below. As described above, the SCF method has advantages and disadvantages.

The STF method will be described next. This method is a method for suppressing an unnecessary signal component based on a factor which is STF (Sign Transit Factor). The STF is an indicator representing the zero cross density in the instantaneous amplitude profile (phase profile) concerning the channel direction. A parameter ci(k) representing characteristics of a change in the instantaneous amplitude profile concerning the channel direction is defined as in the following equation (3):

$$c_i(k) = \begin{cases} +1 & (\text{if } b_i(k) \neq b_{i+1}(k)) \\ 0 & (\text{if } b_i(k) = b_{i+1}(k)) \end{cases} \qquad (3)$$

The above equation (3) corresponds to detection of a zero cross point. ci(k) will be referred to as a polarity change parameter. With the use of this polarity change parameter ci(k), an example of STF serving as an indicator indicating the degree of turbulence of phase is defined as in the following equation (4). Here, A(k) in the following equation (4) is defined by the following equation (5):

$$STF(k) = \left|1 - \sqrt{1 - A(k)^2}\right|^q \qquad (4)$$

$$(0 \leq STF(k) \leq 1)$$

$$A(k) = 1 - \frac{1}{N-1}\sum_{i=1}^{N-1} c_i(k) \qquad (5)$$

In the above equations, N represents the number of receiving channels, and q is a parameter for adjusting the STF. The STF can be computed by using an equation other than the equations (4) and (5). In this case, it is desirable to use a monotonically decreasing function which satisfies $0 \leq STF(k) \leq 1$ and with respect to the zero cross density $1/(N-1) \times \Sigma ci(k)$ (see FIG. 12 which will be described below).

When the phases are identical in all the channels, as zero cross does not occur among individual adjacent channels, the polarity change parameter is 0 and the STF is 1. When the phases are turbulent, on the other hand, as the zero cross density is increased, the STF is decreased. Accordingly, by using the STF to apply weighting processing a reception signal (beam data) having been subjected to the phase alignment and summing processing, it is possible to reduce an unnecessary signal component.

However, it has been recognized from experiments that, when a strong reflector exists, dark portions are generated at positions located at the same depth as the strong reflector and distant from the strong reflector. Further, in some situations, a trend in which the side-lobe reduction effects are insufficient in the vicinity of the strong reflector has been recognized.

(2) Advantages and disadvantages of the two methods

Figure 1:
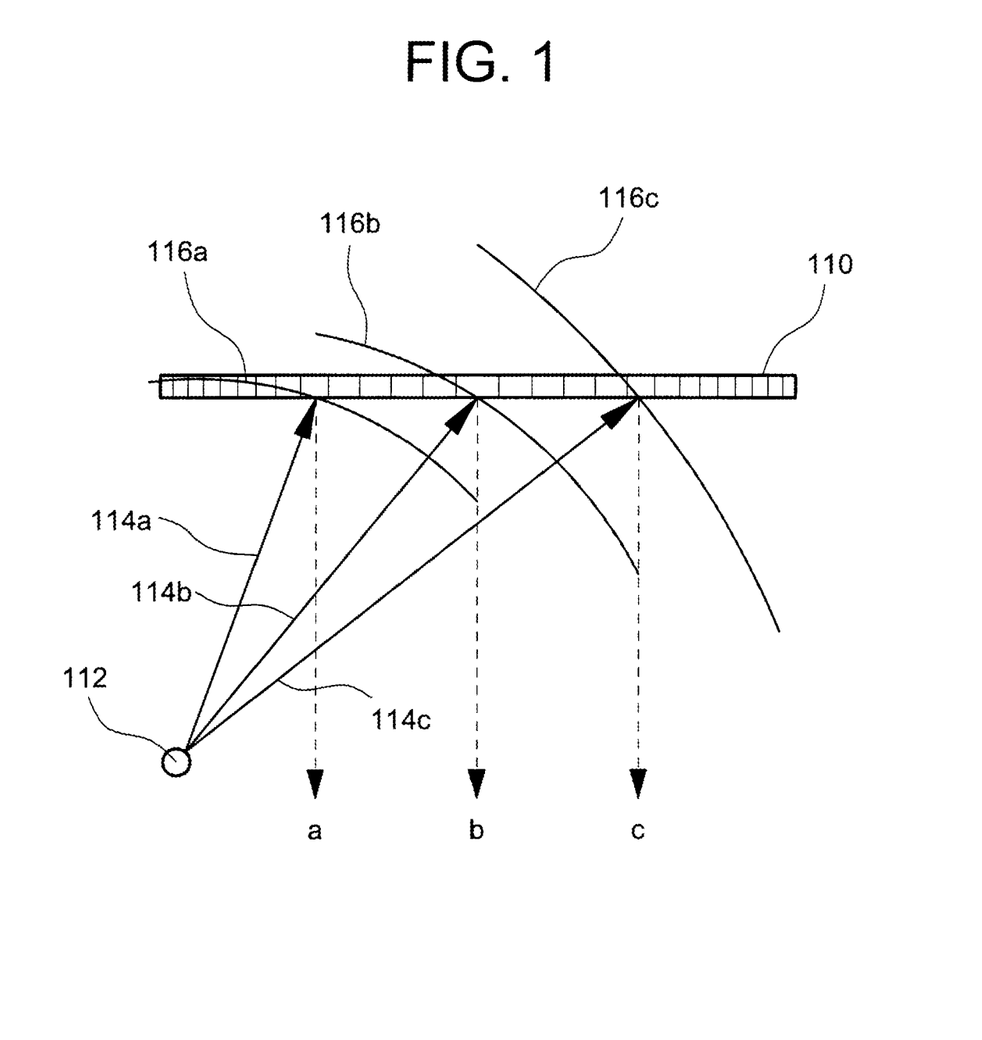
FIG. 1 is a view for explaining a reflection wave from a strong reflector toward an array transducer.

FIG. 1 illustrates a strong reflector (a side-lobe component generation source) and three virtual main beams (main lobe). An array transducer is composed of a plurality of transducer elements. Symbols "a", "b", and "c" represent three main beam positions (center positions), respectively. A strong reflector 112 exists distant from these main beam positions and at a certain depth. Reference numerals 114a, 114b, and 114c represent reflection waves emitted from the strong reflector 112 toward the origins of the respective main beam positions, and reference numerals 116a, 116b, and 116c represent wave surfaces of these reflection waves (e.g., the instantaneous peak of a compression wave). As illustrated in FIG. 1, the further the receiving beam a, b, c, is distant from the strong reflector 112 in the horizontal direction, the greater the inclination of the wave surface 116a, 116b, and 116c of the side-lobe component which is received.

Figure 2:
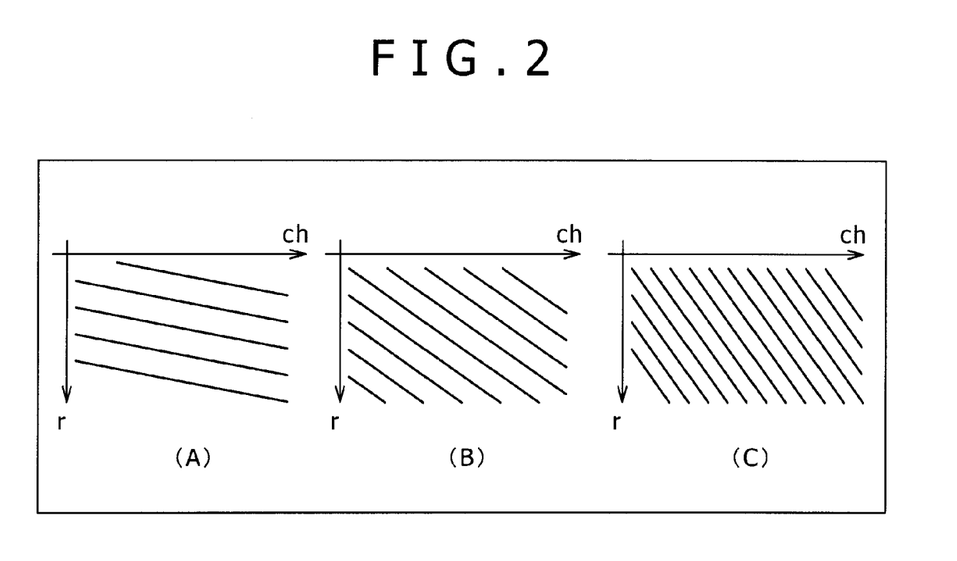
FIG. 2 is a view schematically representing a state of a wave surface of a reflection wave from a strong reflector.

FIG. 2 schematically represents the above-described three wave surfaces as continuous compression waves. In representing each wave surface, the delay processing in a receiving unit is taken into consideration. In FIG. 2, the horizontal axis "ch" indicates the channel direction, and the vertical axis "r" indicates the depth direction. FIG. 2(A) illustrates a wave surface in a case where the distance from the strong reflector to the origin of the main beam position is short, FIG. 2(B) illustrates a wave surface in a case where the distance from the strong reflector to the origin of the main beam position is intermediate, and FIG. 2(C) illustrates a wave surface in a case where the distance from the strong reflector to the origin of the main beam position is long. Observing sign data arrays along the channel direction in these three cases, it is recognized that the greater the inclination of the wave surface, the greater the density of the cross point (sign inversion point) crossing the baseline.

Figure 3:
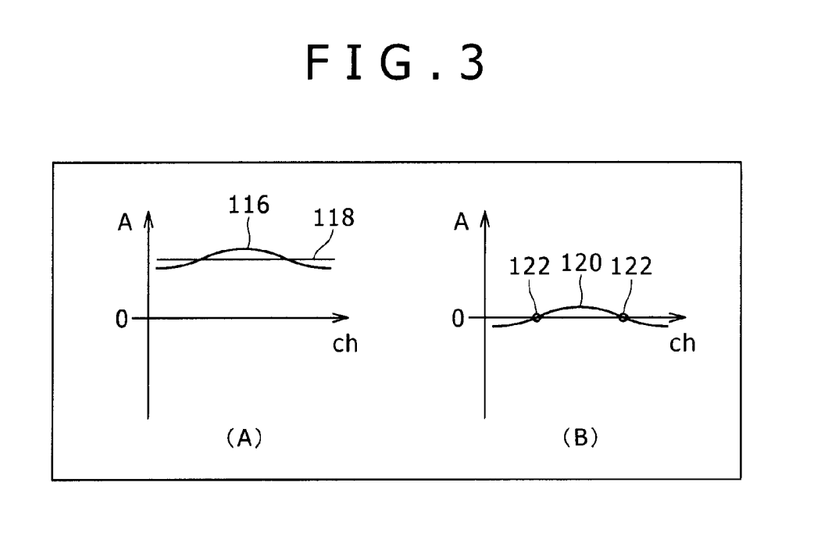
FIG. 3 is a view illustrating an amplitude profile in case 1 and an amplitude profile in case 2.
Figure 4:
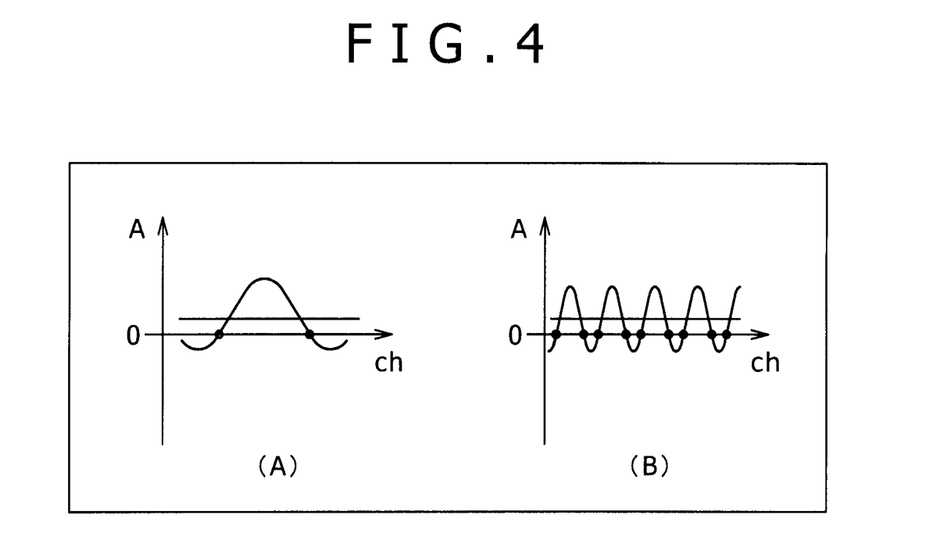
FIG. 4 is a view illustrating an amplitude profile in case 3 and an amplitude profile in case 4.
Figure 5:
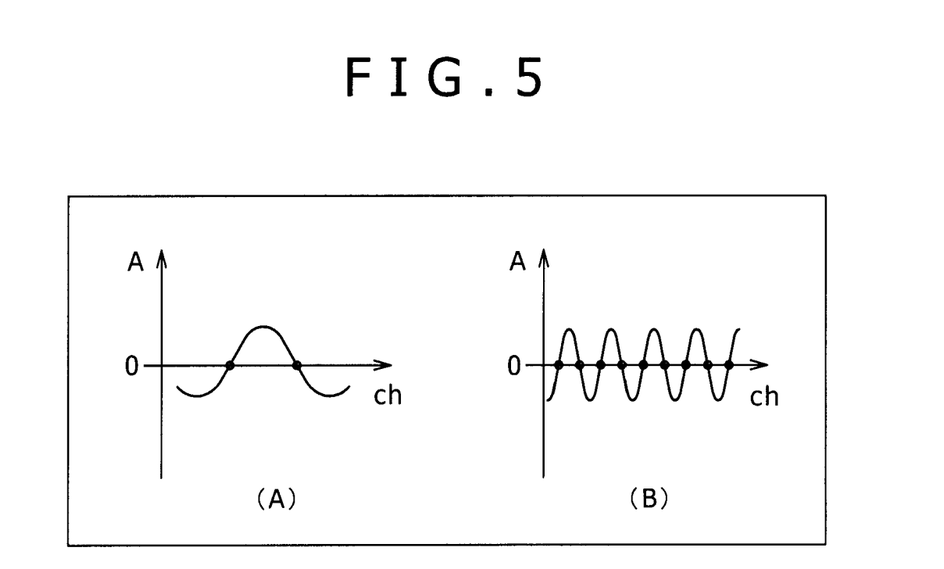
FIG. 5 is a view illustrating an amplitude profile in case 5 and an amplitude profile in case 6.
Figure 6:
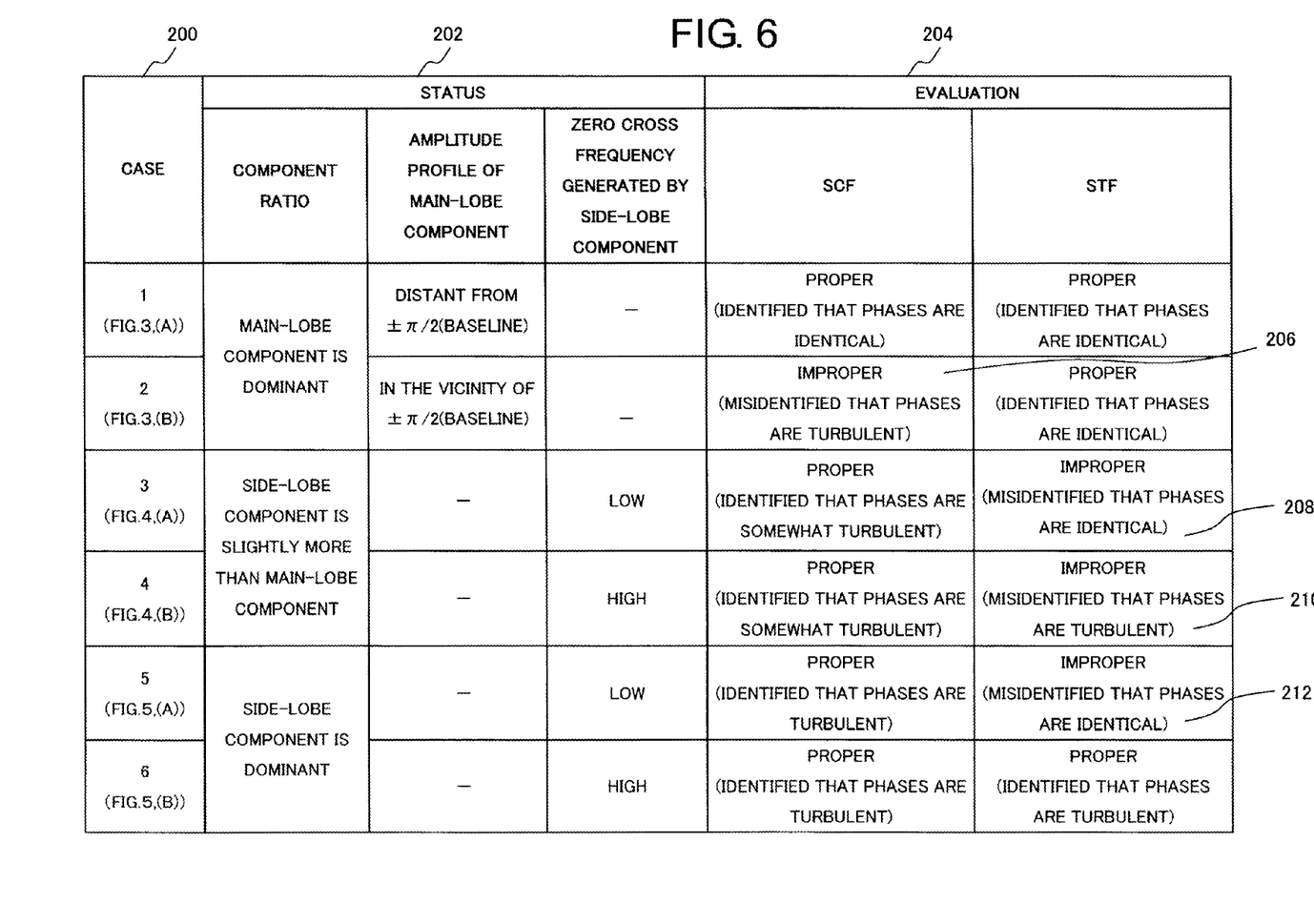
FIG. 6 is a table for explaining an application result of two methods in cases 1 to 6.

FIG. 3 illustrates Case 1 and Case 2 which will be described below; FIG. 4 illustrates Case 3 and Case 4 which will be described below; and FIG. 5 illustrates Case 5 and Case 6 which will be described below. In each of the graphs in FIGS. 3 to 5, the horizontal axis "ch" indicates the channel direction, and the vertical axis "A" indicates amplitude of each channel reception signal having been subjected to delay processing. FIG. 6 is a table in which, concerning Cases 1 to 6 (see reference numeral 200), various situations are described (see reference numeral 202), and whether or not the SCF method and the STF method properly function in each case is evaluated (see reference numeral 204). The advantages and disadvantages of each of the SCF method and the STF method will be specifically reviewed below.

As illustrated in FIG. 3(A), in Case 1, a reflection wave component from the main beam direction (i.e. a main lobe component as an actual signal component) is dominant in a reception signal, and the amplitude profile 116 in the channel direction is distant from the baseline. Reference numeral 118 indicates the average level of the amplitude profile. It should be noted, however, that even in a case in which the main lobe component is dominant, due to effects caused by a shift of the sonic speed which is set on the ultrasonic diagnosis apparatus from the actual sonic speed, an error during the delay processing in the receiving beam former, or the like, in general, the phases are not completely identical among a plurality of channels. In Case 2, as illustrated in FIG. 3(B), the main lobe component is dominant and the amplitude profile 120 is near the baseline. Case 1 and Case 2 are generated when observing a homogeneous medium in which the side-lobe component is hardly mixed, for example, and are repeatedly generated in an alternating manner on the time axis in accordance with arrival of the wave surface. As illustrated in FIG. 6, concerning Case 1, it is determined, in both the SCF method and the STF method, that the phases are substantially identical, because the number of positive sign data items is the maximum and the zero cross density is 0 (minimum value). In this Case 1, proper gain adjustment can be performed by using either one of the SCF method and the STF method. Concerning Case 2, on the other hand, while a variation of the amplitude profiles 120 is actually small, because the amplitude profile 120 crosses the baseline, the number of positive data items and the number of negative data items are substantially the same and, in the case of the SCF method, it is considered that the phases are turbulent (see reference numeral 206). In other words, there is a possibility that misidentification is caused. It is consequently understood that, with the SCF method, the gain adjustment is improper and the uneven phenomenon as described above is generated on the ultrasonic image. With the STF method, on the other hand, as the number of zero cross points 112 on the baseline is small; i.e. as a small zero cross density is detected, the phases can be considered to be identical. As a result, gain adjustment can be performed properly.

In Case 3, as illustrated in FIG. 4(A), the amount side-lobe component is slightly greater than the amount of main-lobe component and also the amplitude profile in the channel direction exhibits a long period (low frequency). Here, the long period (low frequency) represents that the generation source of the side-lobe component is relatively close to the main beam. In Case 4, as illustrated in FIG. 4(B), the amount of the side-lobe component is slightly greater than the amount of main-lobe component and also the amplitude profile in the channel direction exhibits a short period (high frequency). Here, the short period (high frequency) represents that the generation source of the side-lobe component is relatively distant from the main beam. Case 3 and Case 4 correspond to cases in which a homogenous tissue is observed in the field where a side-lobe component is mixed. As illustrated in FIG. 6, in Case 3, a small degree of bias is identified concerning the ratio of existence of the positive sign data and the negative sign data and it is properly determined that the phases are slightly turbulent in the SCF method, and proper gain adjustment can be performed. On the other hand, as the zero cross density is not very large, according to the STF method, it can be improperly determined that the phases are identical (see reference numeral 208). As a result, with the STF method, there is a possibility that the gain adjustment becomes improper. This can be understood to be a cause of poor side-lobe reduction effects in the vicinity of the strong reflector when using the STF method. In Case 4, on the other hand, as illustrated in FIG. 6, there is a bias in the ratio of existence between the positive sign data and the negative sign data and, according to the SCF method, it is properly determined that the phases are turbulent to a small degree, and proper gain adjustment can be performed. However, as the zero cross density is significantly large, with the STF method, it is improperly determined that the phases are turbulent (see reference numeral 210). This can be understood as a cause of generation of dark portions at positions distant from the strong reflector in the STF method.

In Case 5, as illustrated in FIG. 5(A), the side-lobe component is dominant and the amplitude profile in the channel direction exhibits a long period (low frequency). As described above, the long period (low frequency) is an indication that the generation source of the side-lobe component is relatively close to the main beam. In Case 6, as illustrated in FIG. 5(B), the side-lobe component is dominant and the amplitude profile in the channel direction exhibits a short period (high frequency). As described above, the short period (high frequency) is an indication that the generation source of the side-lobe component is relatively distant from the main beam. The side-lobe component in Case 5 and Case 6 is generated in a cavity in a living organism, for example. In Case 5, in which the existence ratio of positive sign data and the existence ratio of negative sign data are substantially the same, according to the SCF method, it is determined that the phases are turbulent and proper gain adjustment can be performed, as illustrated in FIG. 6. On the other hand, as the zero cross density is not very large, according to the STF method, there is a possibility that the phases are misidentified as being identical (see reference numeral 212). This can be understood as a cause of generation of poor side-lobe reduction effects in the vicinity of the strong reflector in the STF method. In Case 6, in which the existence ratio of positive sign data and the existence ratio of negative sign data are substantially the same, it is determined that the phases are turbulent according to the SCF method and proper gain adjustment can be performed, as illustrated in FIG. 6. Further, as the zero cross density is increased, it can be considered that phases are turbulent in the STF method and proper gain adjustment can be performed.

(3) Combination of Two Methods

It is therefore desired to combine the above two methods, to thereby adjust gain of a reception signal.

Reviewing more specifically, several combination methods can be considered. A first combination method is a method in which the SCF method is selected as necessary, as indicated in the following equation (6). Hereinafter, a new indicator generated after the combination will be referred to as NewFactor(k).

$$NewFactor(k) = \begin{cases} C & \text{if } SCF(k) < C \,\&\&\, \text{if } STF(k) \geq D \\ SCF(k) & \text{Other cases} \end{cases} \quad (6)$$

The first combination method is aimed at improving the disadvantages of Case 2 shown in FIG. 6. Specifically, because, in a case in which SCF(k) is less than a predetermined value C and simultaneously STF(k) is a predetermined value D or greater, the evaluation results differ from each other between these two methods; in such a case, NetFactor (k) is fixed to the predetermined value C. In other cases, it is assumed that the evaluation by means of SCF(k) is reliable, and the SCF(k) is adopted directly as NewFactor(k). Here, STF(k) is only used indirectly as reference information for discriminating the cases and is not directly used as a basis for determining NewFactor(k). However, a modification may be made such that STF(k) is directly used entirely or temporarily. Because the SCF method is appropriate except for application to Case 2, this first combination method can be understood as a technique for identifying, based on the STF, a state in which the processing by means of the SCF method is improper, and performing exceptional processing when such a state is determined.

A second combination method defines NewFactor(k) according to the following equation (7):

$$\text{NewFactor}(k) = A \times \text{SCF}(k) + B \times \text{STF}(k)$$

$$(A+B=1, 0 \leq A \leq 1, 0 \leq B \leq 1) \quad (7)$$

The above equation (7) is an equation for performing weighted addition of SCF(k) and STF(k). As, in FIG. 6, concerning Case 2 through Case 5, any disadvantages can be identified in either one of the SCF method and the STF method, such disadvantages of one method are compensated for by the other method. In this case, by varying A, B, the parameter p, which adjusts SCF, and the parameter q, which adjusts STF, the degree of contribution of SCF and STF can be adjusted.

A third combination method defines NewFactor(k) according to the following equation (8):

$$\text{NewFactor}(k) = \sqrt{\text{SCF}(k) \times \text{STF}(k)} \quad (8)$$

With this method, NewFactor(k) is obtained by the geometric mean of SCF and STF. As in the case of the second combination method described above, because, in FIG. 6, any disadvantages can be identified in either one of the SCF method and the STF method concerning Case 2 through Case 5, such disadvantages of one method are compensated for by the other method. With the parameter p, which adjusts SCF and the parameter q, which adjusts STF, the degree of contribution of SCF and STF can be adjusted.

Here, so long as the evaluation value is computed by using the two parameters; i.e., the existence ratio of positive sign and negative sign and the zero cross density, the evaluation value computing equation is not limited to the equations (6) to (8) described above. While the equations (4) and (5) are monotonically decreasing functions with respect to the zero cross density, in order to address the problems caused in Case 4, there may be added processing in which a threshold value of the zero cross density is set and the STF value is fixed when the zero cross density exceeds the threshold value, as will be described below. Further, STF which is thus modified may be combined with SCF.

(4) Structure of Embodiment

Figure 7:
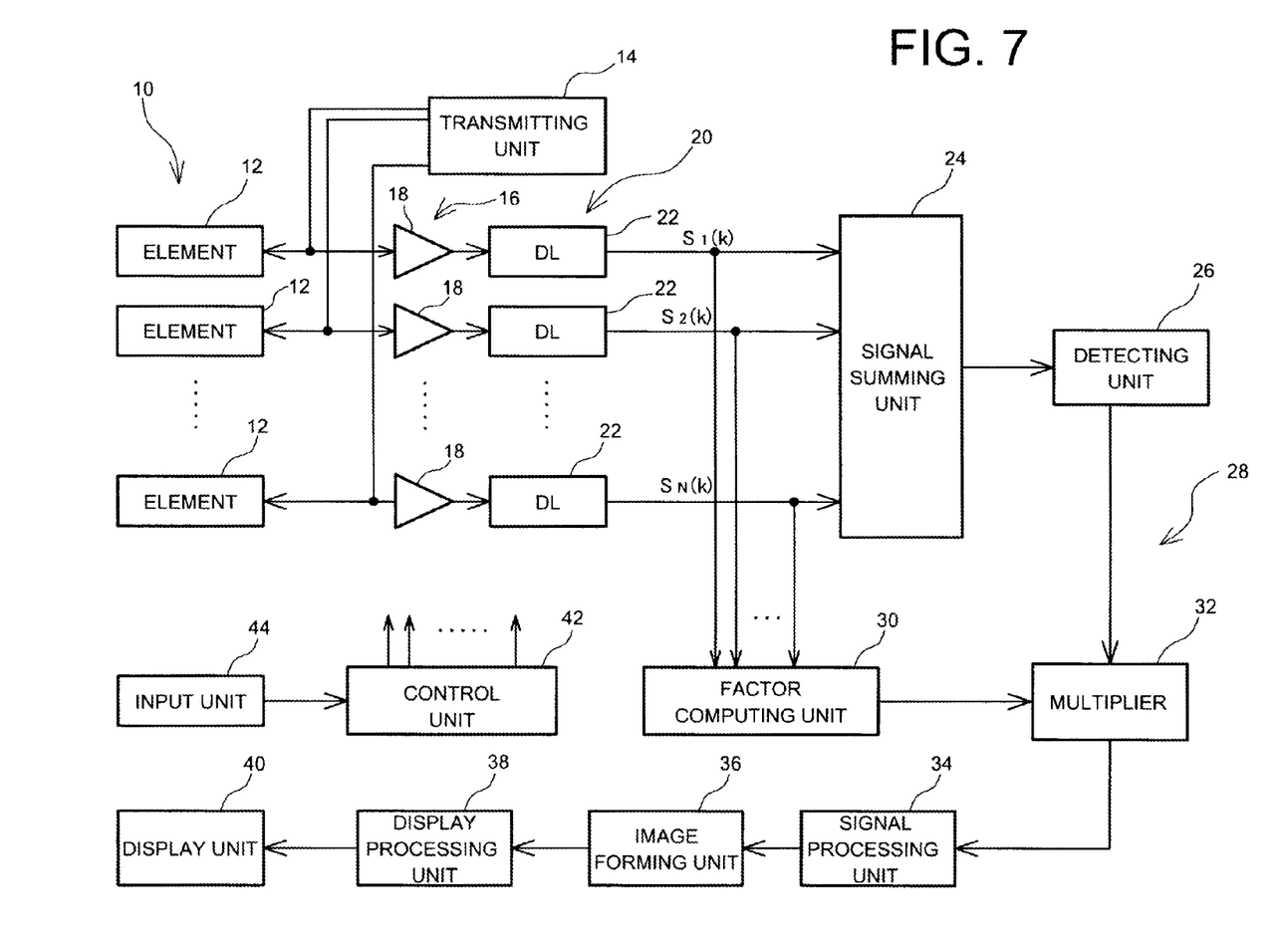
FIG. 7 is a block diagram illustrating an ultrasonic diagnosis apparatus according to an embodiment.

FIG. 7 is a block diagram illustrating a whole structure of a preferable embodiment of an ultrasonic diagnosis apparatus according to the present invention. This ultrasonic diagnosis apparatus is used in the medical field and forms an ultrasonic image based on a reception signal obtained by transmitting and receiving ultrasound with respect to a living organism. While in the present embodiment a B-mode tomographic image is formed as an ultrasonic image, obviously a Doppler image or the like may be formed.

Referring to FIG. 7, an array transducer 10 is disposed within an ultrasonic probe and is composed of a plurality of transducer elements 12 which are arranged in a straight line. Obviously, the transducer elements 12 may be arranged in an arc shape. Ultrasonic beams (transmitting beams and receiving beams) are formed by using the plurality of transducer elements 12 and are electronically scanned. Electronic scanning methods including an electronic sector scanning method, an electronic linear scanning method, or the like are known. A 2D array transducer can be used in place of a 1D array transducer.

A transmitting unit 14 is a transmitting beam former. Specifically, the transmitting unit 14 supplies a plurality of transmitting signals having a predetermined delay relationship to the plurality of transducer elements 12 at the time of transmission. In this manner, transmitting beams are formed. At the time of reception, reflection waves from within the living organism are received by the array transducer 10. In this manner, a plurality of reception signals (element reception signals) are generated and output to an amplification unit 16. The amplification unit 16, a delay unit 20, and a signal summing unit 24 form a receiving unit, which is a receiving beam former.

The amplification unit 16 is composed of a plurality of amplifiers 18. On the downstream side of the amplification unit 16, the delay unit 20 which is composed of a plurality of delay devices 22 which execute delay processing (phase alignment processing) is provided. A delay time, that is delay data, to be supplied to each delay device 22 is supplied from a control unit 42. An apodization processing unit may be provided downstream of the delay unit 20. Each delay device 22 may be formed of a FIFO memory. An A/D converter unit is not shown in the figure. A plurality of reception signals having been subjected to the delay processing (a plurality of element reception signals) are input to the signal summing unit 24, in which these plurality of reception signals are summed to electronically form a receiving beam. The reception signal obtained after the phase alignment and summing processing is output to a detection unit 26, which is a known circuit which performs detection processing. An input unit 44 is connected to the control unit 42.

In the present embodiment, in order to perform suppression of an unnecessary signal component, an unnecessary signal component suppression unit 28 is provided. Specifically, the unnecessary signal component suppression unit 28 includes a factor computing unit 30 and a multiplier 32. The factor computing unit 30 is a circuit which computes a factor (evaluation value) for unnecessary signal component suppression based on a plurality of element reception signals having been subjected to the delay processing but having not yet been subjected to the summing processing. The multiplier 32 executes suppression processing of an unnecessary signal component by using the factor. The multiplier 32 multiplies a reception signal after detection with the factor to suppress (reduce) the reception signal in accordance with the amount of the unnecessary signal component. The reception signal having been subjected to the unnecessary signal component suppression processing is transmitted to a signal processing unit 34. The signal processing unit 34 executes various signal processing operations such as logarithmic transformation and sends the signal after the processing to an image forming unit 36. In the present embodiment, the image forming unit 36 is formed of a digital scan converter (DSC), which forms a B-mode tomographic image. The image data are transmitted to a display device 40 via a display processing unit 38. While in the present embodiment a B-mode image is formed, a two-dimensional blood flow image or the like may be formed. While in the present embodiment multiplication of the factor is performed in the processing of suppressing the unnecessary signal component, other techniques such as subtraction of a signal may be used to suppress or reduce the unnecessary signal component.

It is also possible to apply smoothing processing to a one-dimensional factor array formed of a plurality of factors arranged in the depth direction and provide to the multiplier 32 the factor having been subjected to the smoothing processing. Alternatively, it is also possible to apply two-dimensional smoothing processing to a two-dimensional factor array including factors arranged in the depth direction and the beam scan direction and provide the factor after the smoothing processing to the multiplier 32. With these structures, an abrupt change in image quality can be mitigated.

Figure 8:
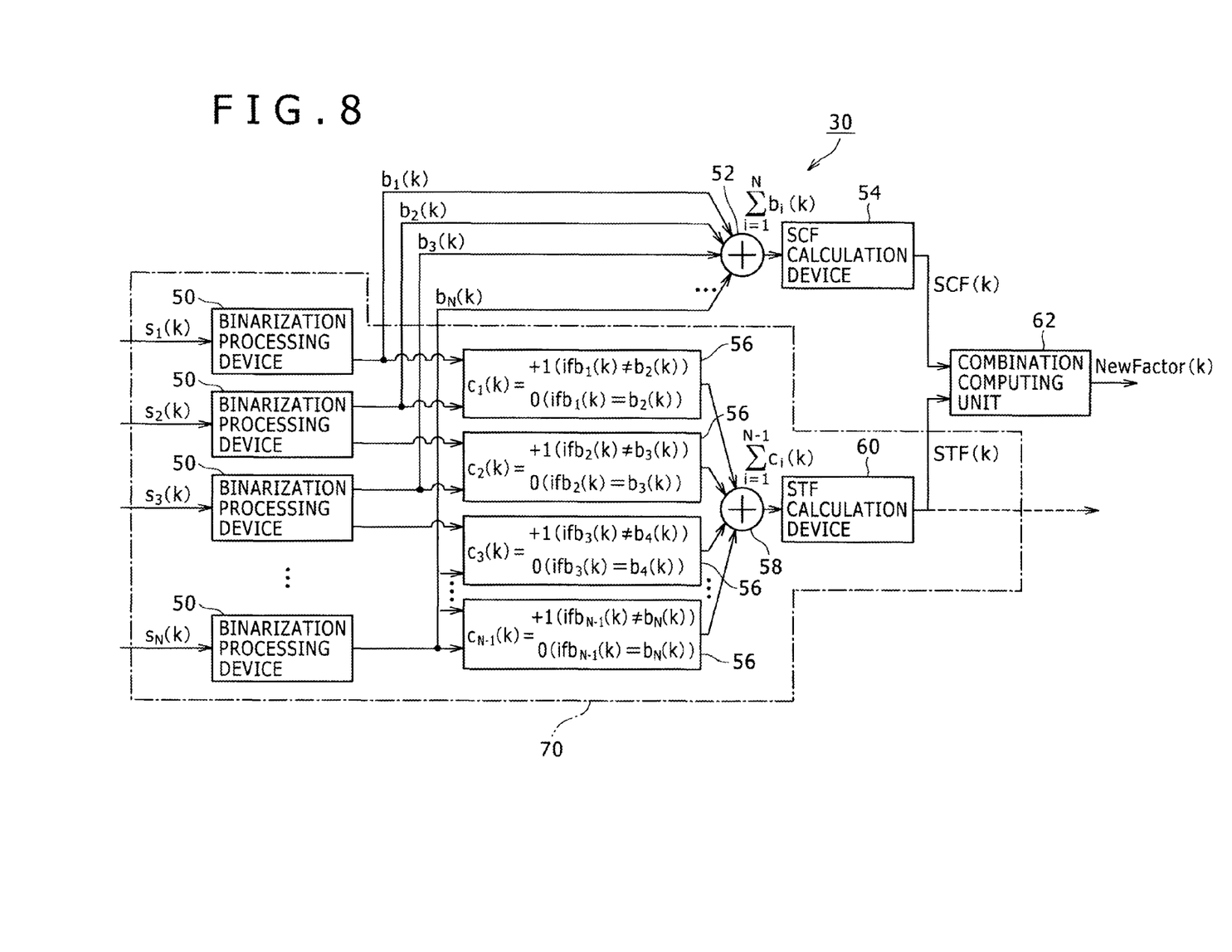
FIG. 8 is a block diagram illustrating a specific example of a factor computing unit.

The specific structure of the factor computing unit 30 will be described. The factor computing unit 30 executes the computation which is already described to compute the factor for unnecessary signal component suppression (NewFactor(k)) to be multiplied by the reception signal having been subjected to the phase alignment and summing processing. The factor computing unit 30 can be roughly divided into a binarization module, an SCF calculation module, an STF calculation module, and a combination computation module.

Referring to FIG. 8, $s1(k)$ to $sN(k)$ represent reception signal arrays after the delay processing. In each binarization processing device 50, a sign bit is extracted. A plurality of sign bits which are extracted are designated by $b1(k)$ to $bN(k)$. Here, binarization processing may be performed with respect to the sign bit. The plurality of sign bits $b1(k)$ to $bN(k)$ are summed by an adder 52 to obtain a summed value, and an SCF calculation device 54 computes the SCF based on the summed value (see equation (2) described above). In each block 56, sign transit is detected between adjacent signals (adjacent sign bits). Specifically, when polarity inversion occurs between two signal bits which are adjacent to each other in the channel direction, the polarity change parameter $ci(k)$ is +1, whereas when the polarity remains unchanged, the polarity change parameter $ci(k)$ is 0. These values are summed in an adder 58 to generate a summed value. An STF calculation device 60 is a circuit which computes the STF based on equations (4) and (5) described above. It is desirable to provide a one-dimensional or two-dimensional smoothing circuit after the adder 58 or after the STF calculation device 60. While in the illustrated example inversion of the sign bit between adjacent elements is detected, inversion of the sign bit among a plurality of elements discretely selected from a plurality of elements may be detected.

A combination computing unit 62 computes a factor for gain adjustment (NewFactor(k)) based on SCF(k) and STF(k) for each depth k which is described above. The factor (NewFactor(k)) is then output to the multiplier 32. It is possible to install only a module 70 illustrated in FIG. 8 in an ultrasonic diagnosis apparatus. In other words, depending on the status of the ultrasonic diagnosis, only the STF method may be used. In this case, the STF is output to the multiplier as indicated by a broken line in FIG. 8. It is also possible to use the STF method in combination with a third method other than the SCF method.

Figure 9:
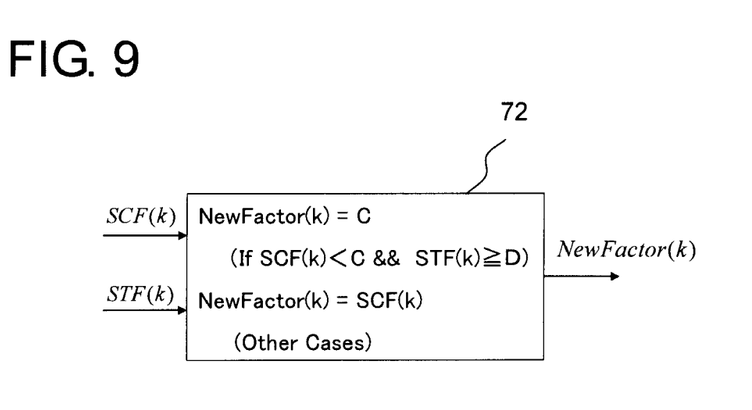
FIG. 9 is a block diagram illustrating a first specific example of a combination computing unit.
Figure 10:
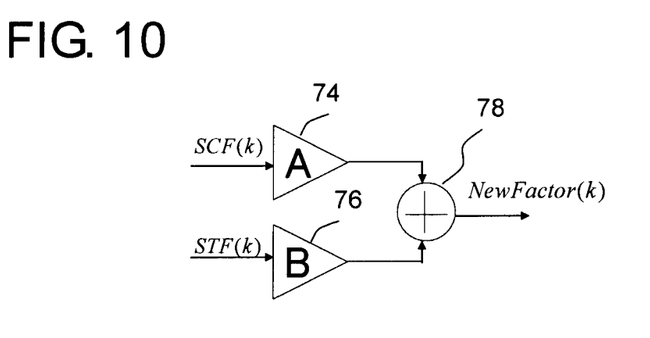
FIG. 10 is a block diagram illustrating a second specific example of a combination computing unit.
Figure 11:
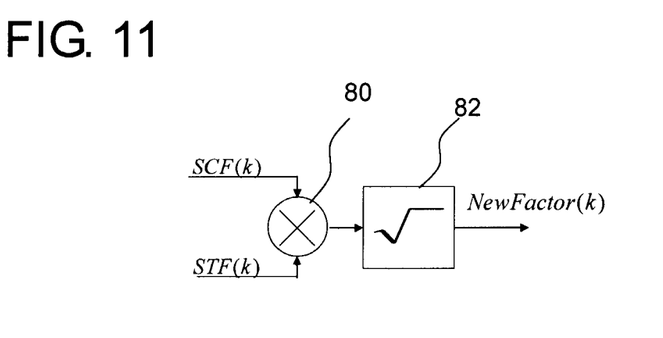
FIG. 11 is a block diagram illustrating a third specific example of a combination computing unit.

Several specific examples of the combination computing unit 62 illustrated in FIG. 8 are illustrated in FIGS. 9 to 11. In a block 72 illustrated in FIG. 9, the factor NewFactor(k) is computed according to equation (6) described above. With this structure, the factor is specified based on case discrimination. In the structure illustrated in FIG. 10, the factor NewFactor(k) is computed according to equation (7) described above. With this structure, the factor is computed based on weight average. A circuit 74 multiplies SCF by a weight A and a circuit 76 multiplies STF by a weight B, and these two multiplication results are added by an adder 78. In the structure illustrated in FIG. 11, the factor NewFactor(k) is computed according to equation (8) described above. With this structure, the factor is computed based on geometric mean. A multiplier 80 multiplies SCF and STF, and a block 82 computes a square root of the multiplication result. The block 82 is formed of an operator or a memory (table).

Figure 12:
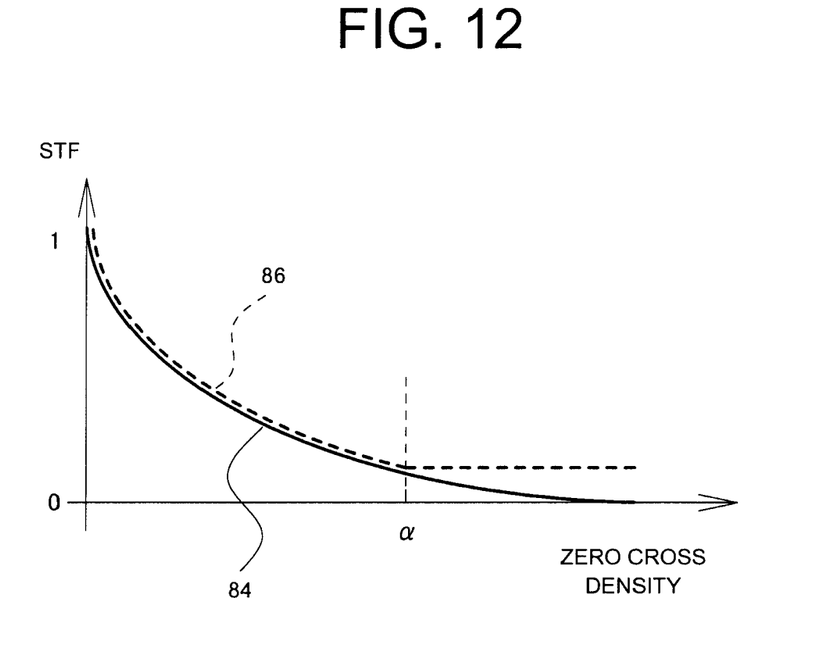
FIG. 12 is a view illustrating an STF determination curve.

FIG. 12 illustrates an STF determination curve. In FIG. 12, the horizontal axis indicates the zero cross density and the vertical axis indicates STF. While, as indicated by solid line 84, a general monotonically decreasing function can be used, when the zero cross density is greater than a fixed value α (when the STF computation result is smaller than the fixed value), the STF may be fixed to a predetermined value, as indicated by broken line 86. Such a modification can be applied to the various structures described above.

(5) Additional Notes

The STF method described above is a new method which is valuable even when used by itself. The present application also includes the following invention:

(i) An ultrasonic diagnosis apparatus including a plurality of transducer elements which transmit and receive ultrasound, a delay processing unit which performs delay processing with respect to a plurality of element reception signals output from the plurality of transducer elements, a summing processing unit which performs summing processing with respect to the plurality of element reception signals having been subjected to the delay processing to generate a reception signal, a factor computing unit which computes a factor for use in reduction of an unnecessary signal component, based on an arranging direction of sign bits and the number of sign inversion of sign bits in a sign data array formed of a plurality of sign bits that are extracted from the plurality of element reception signals having been subjected to the delay processing but having not been subjected to the summing processing, and a gain varying unit which changes gain of the reception signal having been subjected to the summing processing, based on the factor.

(ii) In the apparatus as described in above (i), the factor computing unit includes a counting unit which counts the number of sign inversion events that occur between adjacent sign bits in the sign bit array, and a standardization computing unit which computes the factor by dividing the number of sign inversion events by the number of sign bits forming the sign bit array.

(iii) In the apparatus as described in above (ii), the factor computing unit generates the factor such that gain of the reception signal is low when a frequency of occurrence of the sign inversion events is high, and generates the factor such that gain of the reception signal is high when the frequency of occurrence of the sign inversion events is low.

(iv) In the apparatus as described in above (iii), the factor is computed for each depth along each beam direction, there is provided a unit which applies one-dimensional smoothing processing to a plurality of factors arranged in the beam direction or applies two-dimensional smoothing processing to a plurality of factors arranged in the beam direction and a beam arranging direction, and the gain of the reception signal is controlled by using a factor having been subjected to the smoothing processing.

While the preferred embodiment of the present invention has been described using specific terms, such description is for illustrative purposes only, and it is to be understood that changes and variations may be made without departing from the spirit or scope of the appended claims.

What is claimed is:

1. An ultrasonic diagnosis apparatus comprising:
   an array transducer which comprises a plurality of transducer elements;
   a receiving beam former which performs delay processing with respect to a plurality of element reception signals output from the plurality of transducer elements, and which performs summing processing with respect to the plurality of element reception signals having been subjected to the delay processing;

a factor computing unit which computes an evaluation value based on a sign data array formed of a plurality of sign data items arranged in a same direction as the plurality of transducer elements, the plurality of sign data items having been extracted from the plurality of element reception signals which have been subjected to the delay processing but which have not been subjected to the summing processing, and the factor computing unit computing the evaluation value based on a first factor and a second factor which are computed from the sign data array; and a gain adjustment unit which adjusts gain of a reception signal having been subjected to the summing processing, by using the evaluation value, wherein the first factor represents a level of sign coherence in the sign data array, and wherein the second factor represents a sign transit density in the sign data array.

2. The ultrasonic diagnosis apparatus according to claim 1, wherein the factor computing unit includes:
- a first factor computing unit which computes the first factor with reference to the sign data array;
- a second factor computing unit which computes the second factor with reference to the sign data array; and
- an evaluation value computing unit which computes the evaluation value based on the first factor and the second factor.

3. The ultrasonic diagnosis apparatus according to claim 2, wherein the first factor computing unit and the second factor computing unit operate in parallel.

4. The ultrasonic diagnosis apparatus according to claim 2, wherein the evaluation value computing unit computes the evaluation value by performing weighted addition processing using the first factor and the second factor.

5. The ultrasonic diagnosis apparatus according to claim 1, wherein the evaluation value computing unit computes the evaluation value by performing multiplication processing using the first factor and the second factor.

6. The ultrasonic diagnosis apparatus according to claim 1, wherein in a specific case in which the first factor is smaller than a first threshold value and the second factor is greater than a second threshold value, the evaluation value computing unit determines, as the second factor, a value which is based on the second factor, or a predetermined value.

7. The ultrasonic diagnosis apparatus according to claim 1, wherein the evaluation value computing unit computes the evaluation value in accordance with a dynamic change of a depth of a receiving sample point in real time, for each depth of the receiving sample point.

8. An ultrasonic diagnosis apparatus comprising, an array transducer which comprises a plurality of transducer elements;

a receiving beam former which performs delay processing with respect to a plurality of element reception signals output from the plurality of transducer elements, and which performs summing processing with respect to the plurality of element reception signals having been subjected to the delay processing;

a factor computing circuit which computes an evaluation value based on a sign data array formed of a plurality of sign data items arranged in a same direction as the plurality of transducer elements, the plurality of sign data items having been extracted from the plurality of element reception signals which have been subjected to the delay processing but which have not been subjected to the summing processing, and the factor computing circuit computing the evaluation value based on a first factor and a second factor which are computed from the sign data array; and a multiplier which adjusts gain of a reception signal having been subjected to the summing processing, by using the evaluation value, wherein the first factor represents a level of sign coherence in the sign data array, and wherein the second factor represents a sign transit density in the sign data array.

* * * * *